United States Patent [19]

Chretien et al.

[11] Patent Number: 5,750,501
[45] Date of Patent: May 12, 1998

[54] METHOD AND COMPOSITION FOR TREATMENT OF PATIENTS HAVING DECOMPENSATED LIVER DISEASE

[75] Inventors: Paul B. Chretien, Rockville, Md.; Milton G. Mutchnick, West Bloomfield, Mich.

[73] Assignees: Alpha 1 Biomedicals, Inc., Bethesda, Md.; The Board of Governors of Wayne State Univ., Detroit, Mich.

[21] Appl. No.: 313,160

[22] PCT Filed: Nov. 5, 1993

[86] PCT No.: PCT/US93/10619

§ 371 Date: Sep. 26, 1996

§ 102(e) Date: Sep. 26, 1996

[87] PCT Pub. No.: WO95/12405

PCT Pub. Date: May 11, 1995

[51] Int. Cl.$^6$ ............................................ A61K 38/00
[52] U.S. Cl. ............................ 514/12; 530/324; 530/399
[58] Field of Search ............................ 514/12; 530/324, 530/399

[56] References Cited

U.S. PATENT DOCUMENTS 5,308,833  5/1994  Scharschmidt .................... 514/12

Primary Examiner—Cecilia J. Tsang
Assistant Examiner—P. Lynn Touzeau
Attorney, Agent, or Firm—Rothwell, Figg, Ernst & Kurz, p.c.

[57] ABSTRACT

A method and composition for treating a Hepatitis B patient having hepatic decompensation utilizes Hepatitis B virus-reducing amounts of $T\alpha_1$, administered to a patient having decompensated liver disease so as to render the patient seronegative for Hepatitis B virus DNA.

8 Claims, No Drawings

METHOD AND COMPOSITION FOR TREATMENT OF PATIENTS HAVING DECOMPENSATED LIVER DISEASE

BACKGROUND OF THE INVENTION

1. Field of the Invention

The present invention relates to a method and composition for treating patients having hepatic decompensation.

2. Description of the Background Art

Hepatic decompensation is liver failure which can result from chronic or chronic active infection of a patient by Hepatitis B virus.

Of several known therapeutic agents which have been proposed for use in the treatment of Hepatitis B, the most extensively evaluated is interferon alpha-2b (hereinafter "α-interferon"), available commercially as INTRON® A. Unfortunately, the response rate of chronic Hepatitis B patients to α-interferon has been less than 50%. With the establishment of liver transplantation as a therapeutic modality for a variety of liver diseases, new expectations were raised for a cure of hepatic decompensation resulting from Hepatitis B infection. Unfortunately after some years of experience with liver transplantation, it is apparent that the rate of reoccurrence of Hepatitis B infection following transplantation is high.

In patients who have undergone liver transplantation wherein Hepatitis B virus DNA was detectable in the patient's serum prior to transplantation, the recurrence of Hepatitis B infection has been virtually universal within one year following transplantation. In view thereof, current medical practice precludes liver transplantation at many transplant centers in patients who have chronic Hepatitis B infection and who are serum positive for Hepatitis B virus DNA.

Treatment with α-interferon has not been successful in rendering serum of most patients with decompensated chronic Hepatitis B liver disease negative for Hepatitis B virus DNA. In fact, the INTRON® A label insert warns that α-interferon is contraindicated for patients exhibiting symptoms of hepatic failure, and may actually increase the risk of clinical decompensation. It is also known that α-interferon can lead to a level of decompensation which results in death.

In addition to α-interferon, another drug which has been suggested for treatment of Hepatitis B in patients is Thymosin $\alpha_1$ ("T$\alpha_1$"). However, in view of the published warnings concerning the increased risk of hepatic decompensation when treating Hepatitis B using α-interferon, there would appear to be a negative motivation to use Thymosin $\alpha_1$ in patients exhibiting symptoms of decompensated liver disease.

There remains a need in the art for methods of treating patients with hepatic decompensation so as to qualify such patients for liver transplantation.

SUMMARY OF THE INVENTION

In accordance with the present invention a method of treating a Hepatitis B patient having hepatic decompensation comprises administering Hepatitis B virus-reducing amounts of T$\alpha_1$ to a patient having decompensated liver disease, so as to render said patient serum negative (seronegative) for Hepatitis B virus DNA.

The invention further includes a composition for use in treating a Hepatitis B patient having hepatic decompensation, comprising a pharmaceutical dosage unit containing a Hepatitis B virus-reducing amount of T$\alpha_1$, which pharmaceutical dosage unit can be administered to Hepatitis B-infected patient having decompensated liver disease, so as to render serum of said patient negative for Hepatitis B virus DNA.

DESCRIPTION OF THE PREFERRED EMBODIMENTS

It has surprisingly been discovered that Thymosin $\alpha_1$ ("T$\alpha_1$") can render Hepatitis B patients having decompensated liver disease serum negative for Hepatitis B virus DNA, thereby qualifying such patients for liver transplantation. This is surprising since the only approved drug for treatment of Hepatitis B, α-interferon, is contraindicated for use in patients with decompensated liver disease.

The terms "Thymosin $\alpha_1$", "Thymosin alpha 1" and "T$\alpha_1$" as used herein encompass not only native (i.e., naturally occurring) T$\alpha_1$ but also synthetic T$\alpha_1$ and recombinant T$\alpha_1$ having the amino acid sequence of native T$\alpha_1$, amino acid sequences substantially similar thereto, or an abbreviated sequence from thereof, and their biologically active analogs (including muteins) having substituted, deleted, elongated, replaced, or otherwise modified sequences which possess bioactivity substantially similar to that of T$\alpha_1$.

Hepatitis B virus-reducing amounts of Thymosin $\alpha_1$ are included within the dosage range of 0.4–4 mg.

Hepatitis B patients having decompensated liver disease are administered Thymosin $\alpha_1$ until the patients are serum negative for Hepatitis B virus DNA, i.e., patients who become seronegative for Hepatitis B virus DNA in two consecutive monthly tests. A test for serum Hepatitis B virus DNA can be any suitable test, for example a radioimmunoassay, such as is available from Abbott Laboratories.

In particularly preferred embodiments, Thymosin $\alpha_1$ is administered by subcutaneous injection twice weekly in pharmaceutical dosage units within the range of about 1–4 mg (e.g., about 1.6 mg). However, it is to be understood that pharmaceutical dosage units containing Thymosin $\alpha_1$ may be formulated in any suitable manner for administration by any suitable route. Suitable routes of administration may include, but are not limited to, parenteral (including subcutaneous, intramuscular, intravenous and intradermal), oral, and transdermal. Particularly preferred embodiments utilize parenteral administration.

In preferred embodiments, T$\alpha_1$ is administered in separate pharmaceutical dosage units. The pharmaceutical dosage units of the present invention include one or more pharmaceutically acceptable carriers and optionally other therapeutic ingredients. The carrier(s) are "acceptable" in the sense of being compatible with the other ingredients of the dosage unit formulation and not deleterious to the recipient thereof.

The pharmaceutical dosage unit formulations may be prepared by any suitable methods.

Such methods may include the step of separately bringing into association the T$\alpha_1$ active ingredient with its carrier, which may comprise one or more ingredients. In general, the formulations are prepared by uniformly and intimately bringing into association the T$\alpha_1$ active ingredient with liquid carriers or finely divided solid carriers or both. Solid dosage unit formulations also may include the step of shaping the product.

Formulations of the present invention suitable for oral administration may be presented as discrete units such as capsules, cachets or tablets, containing a predetermined amount of the $T\alpha_1$ active ingredient; as a powder or granules; as a solution or a suspension in an aqueous liquid or a non-aqueous liquid; or as an oil-in-water liquid emulsion or a water-in-oil liquid emulsion, etc.

A tablet may be made by compression or molding, optionally with one or more accessory ingredients. Compressed tablets may be prepared by compressing, in a suitable machine, free-flowing powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. Tablets may optionally be coated or scored and may be formulated so as to provide slow or controlled release of the active ingredient therein.

Formulations suitable for parenteral administration include aqueous and non-aqueous sterile injection solutions which may optionally contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Suitable dosage units of $T\alpha_1$ can be administered to the patient daily, one or more times per day, e.g., two or three times per day, and doses can be administered one or more days per week, e.g., two, three, four, five, six or seven days per week.

After the patient becomes serum negative for Hepatitis B virus DNA, the decompensated liver of the patient can be removed, and a healthy liver then can be transplanted into the patient.

The invention is further illustrated by the following examples, which are not intended to be limiting.

EXAMPLE 1

Patient 1 is a 48 year old physician who contracted hepatitis B surface antigen (HBsAg) positive hepatitis following a needle stick injury. Approximately 13 years later, liver biopsy showed chronic active hepatitis and cirrhosis. He suffered from significant fatigue. He had ascites and other manifestations of cirrhosis. Liver enzymes were elevated. Standard serologic studies were unusual in that Hepatitis B virus DNA, HBeAg, and HBsAg appeared negative. However, Hepatitis B virus DNA by the more sensitive PCR (polymerase chain reaction) assay was positive, as was Hepatitis B DNA testing of liver tissue obtained at biopsy. He was considered to have a mutant form of Hepatitis B virus infection. He failed to respond to α-interferon.

In an attempt to cure his Hepatitis B infection so that he would be eligible for transplant, he was started on Thymosin alpha 1 at a dose of 1.6 mg subcutaneously twice weekly. After approximately 3 months, he reported less fatigue. After roughly 6 months, Hepatitis B DNA PCR was negative. He had a liver transplant and returned to work shortly after his transplant. At his latest clinic visit, he was feeling well without elevations of his aminotransferase enzymes.

EXAMPLE 2

Patient 2 was a 69 year old man with very far-advanced cirrhosis secondary to long-standing chronic Hepatitis B infection. His findings included jaundice, weakness, severe encephalopathy, hepato-renal syndrome with renal failure, and portal gastropathy secondary to increased portal vein pressure. He received Thymosin alpha 1 at a dose of 1.6 mg subcutaneously twice weekly under a compassionate use protocol in an attempt to cure his Hepatitis B virus infection so that he could received a liver transplant. He tolerated therapy well, and had no side effects, but died from gastric bleeding, renal failure, and encephalopathy after 3½ weeks of therapy. Death was associated with complications of portal hypertension and cirrhosis, and not due to therapy with Thymosin alpha 1.

EXAMPLE 3

Patient 3 was a 53 year old man with chronic Hepatitis B infection, cirrhosis, and esophageal varices. He also had a hepatoma, which recurred after a partial liver resection. Because of the limited amount of remaining normal hepatic tissue, another curative resection was not possible, and the patient's only hope for a cure was a transplant. However, he was not a candidate because of active infection with Hepatitis B.

He was started on Thymosin alpha 1 at a dose of 1.6 mg subcutaneously twice weekly, with the intention of treating him for 26 weeks. He tolerated therapy well and had no adverse effects. However, his therapy was discontinued after 46 injections because of complications of the cirrhosis. He expired about three weeks after his last injection. His death was attributed to bleeding esophageal varices and hepatoma. His hepatologist did not believe that Thymosin alpha 1 contributed to his death.

In summary, the above three patients with cirrhosis and hepatic decompensation received Thymosin alpha 1 at a dose of 1.6 mg subcutaneously twice weekly for periods varying from 3.5 weeks to 6 months. In each case, the intent of therapy was to cure chronic Hepatitis B virus infection so that the patient could be considered for transplant. None of the patients reported any adverse effects due to $T\alpha_1$. One of these patients had resolution of Hepatitis B virus infection while receiving Thymosin alpha 1, and later had a successful liver transplant, with no evidence of re-infection of the transplant by HBV. Two other patients, both of whom had far-advanced disease, died of complications of cirrhosis, with no evidence that Thymosin alpha 1 contributed to their deaths.

EXAMPLE 4

In a clinical trial, Hepatitis B virus (HBV) DNA positive patients, otherwise eligible for liver (OLT) transplant, will be enrolled. Patients will be recruited form the population of patients having end-stage liver disease, and Hepatitis B, and who present themselves for treatment.

CANDIDACY FOR TRANSPLANTATION will be defined as liver failure evidenced by cirrhosis, and some combination of medical factors, as shown below.

Cirrhosis will be diagnosed on biopsy (where practical) or where a biopsy is contraindicated, the diagnosis will be made clinically and confirmed radiographically prothrombin time greater than 16 seconds (normal is 12 seconds)

total bilirubin greater than 2.5 mg % (normal is less than 1 mg %)

serum albumin less than 3 mg % (normal is 3.5–5.5 mg %)

ascites unresponsive to medical management past history of spontaneous bacterial peritonitis liver volume less than 1000 cc (normal is greater than 1400 cc)

variceal hemorrhage hepatic encephalopathy patient is willing and able to abstain from use of alcohol

INCLUSION CRITERIA FOR TRANSPLANT ELIGIBLE PATIENTS end-stage liver disease qualifying patient for orthotopic liver transplant (OLT), demonstrated serum HBV DNA by radioimmunoassay (Abbott Laboratories), documented by 2 determinations at least 1 month apart, with or without elevation of serum transaminase levels, histologic evidence of hepatitis B and cirrhosis (preferably within 6 months); a liver biopsy will be performed if the patient presents a platelet count greater than 70,000 and a prothrombin time less than 3 seconds over control.

ELISA test for HIV-antibody performed on all patients enrolled in study, with any positive result confirmed by Western Blot (2 or more bands)

negative 2nd generation RIBA test for hepatitis C pregnancy test (urine) for women of child bearing age written informed consent.

EXCLUSION CRITERIA FOR TRANSPLANT ELIGIBLE PATIENTS concomitant or prior history of malignancy other than curatively treated skin cancer or surgically cured in situ carcinoma of the cervix end-stage liver disease with clinically significant hepatic encephalopathy, such that the patient cannot provide meaningful informed consent significant acute bleeding, requiring transfusion, within ten (10) days of enrollment multi-organ failure requiring ventilatory support or dialysis vasopressor dependent hemodynamic instability patient has previously received an organ transplant diagnosis of hepatitis C by 2nd generation RIBA test medical-surgical complications requiring intensive care management pregnancy, as documented by a urine pregnancy test active intravenous drug abuse within a period of 2 years Interferon-alpha therapy, including any course equal to or greater than 16 weeks duration, within 12 months of enrollment; Interferon-alpha therapy, including any course less than 16 weeks duration, within 6 months of enrollment patient has received immunosuppressive drug(s), other than corticosteroid drugs, within 6 months of enrollment.

failure to provide written informed consent if patient is female of child bearing age, has not provided agreement to practice birth control if patient is female, has not provided agreement to avoid use of oral contraceptives sepsis evidence to suggest alternative (to hepatitis B) causes of chronic liver disease failure to meet any of the inclusion criteria above.

STUDY DESIGN

This is a study to examine the role of Thymosin alpha 1 injections in achieving or accelerating the loss of serum HDV-DNA. Primary outcome measures are the proportion of patients losing serum HBV DNA during the study. At the time of entry, all study patients will have detectable levels of serum HBV DNA in a minimum 2 consecutive tests.

Before being considered for OLT, each patient will participate in a study using the design described by Simon (Simon R., "Optimal two-stage designs for Phase II clinical trials," Controlled Clinical Trials 10:1–10 (1989)). Simon's design tests the null hypothesis that the success probability has attained an "interesting target" against the alternative that is has attained a "desirable target". "Success" is defined as a living patient who has lost viral DNA by one (1) year after study entry. The desirable target has been set at 0.30, i.e. a 30% success rate. An appropriate value for the uninteresting target depends upon estimation of the one-year of spontaneous loss of viral DNA in patients not treated with thymosin or another anti-viral agent.

PATIENT MONITORING, MANAGEMENT, AND EVALUATION

A population of patients having cirrhosis and serologic markers for hepatitis B virus infection will be entered into the study. These patients are currently excluded as OLT candidates because of their high disease recurrence rate. All enrolled patients who become negative for HBV DNA in 2 consecutive tests will be reevaluated for OLT.

Clinical Protocol

Thymosin Therapy

Thymosin alpha 1, injection will be self-administered, twice weekly, by the subcutaneous route (a patient dose of 1.6 mg per injection)

Patients will be instructed at the time of enrollment in reconstitution of the freeze dried thymosin single-dose, and in self-administration of the investigational drug.

Investigational drug and Water For Injection, USP (solvent) will be dispensed to patients.

The duration of Thymosin alpha 1 injection therapy in the clinical protocol will be (a) if no clinical end-point (resolution of serum HBV DNA) is reached: 12 months;

(b) if the clinical end-point is reached in a period of 12 months or less, then thymosin therapy ends when the patient has been reevaluated and has received a transplant; or (c) if the clinical end-point is reached in a period of 12 months or less, then thymosin therapy ends when the patient has been reevaluated and is considered currently ineligible for transplant.

Concomitant Medications (common)

antacid diuretic(s)

H2 antagonist Lactulose

Patient Monitoring

Patients will be seen (physical examination) once each week for the first month of treatment, twice each month for the second month of treatment, and monthly for the remainder of the period of thymosin therapy.

Patients who do not clear HBV DNA will be seen for follow-up at monthly intervals for a period of six (6) months, after receiving the last dose of Thymosin alpha 1 injection.

Clinical Laboratory Monitoring

A liver biopsy will be performed if all of the following criteria are met: (a) the patient is not referred to transplant, (b) six (6) months subsequent to termination of thymosin therapy, and (c) if the patient presents a platelet count greater than 70,000 and a prothrombin time less than 3 seconds over control. Liver biopsy tissue will, wherever possible, be frozen in liquid Nitrogen for future analysis of HBV DNA by molecular hybridization assay.

HBV DNA by radioimmunoassay (Abbott Laboratories) will be performed at enrollment (time 0) and once monthly throughout therapy and follow-up.

The following routing clinical laboratory analyses will be performed at time of entry and every second week for the initial month of treatment, and will be performed monthly for the remainder of the period of therapy and follow-up.

| | |
|---|---|
| BUN | serum total protein |
| serum creatinine | serum albumin |
| serum glucose | CBC |
| serum cholesterol | WBC |
| serum uric acid | differential count |
| serum Calcium | PLT |
| serum phosphate | PT,PTT |
| alkaline phosphate | urinalysis |
| total bilirubin | direct bilirubin |
| serum Sodium, Potassium, chloride, $CO_2$ | |
| ALT | AST |
| GGTP | |

The following non-routine clinical laboratory analyses will be performed at time of entry, and at month 3, month 6 and month 12; and in the last month of follow-up (month 18).
TSH, FTI
serum protein electrophoresis
autoimmune markers: ASMA, ANA, AMA
hepatitis B serology: sAg/Ab, eAg/Ab, core Ag/Ab CD4+, CD8+, ratio will be determined at time of entry, and at month 6 and month 12; and in the last month of follow-up (month 18)

Serum triglycerides and fractional cholesterol will be determined at the time of entry, and at month 12; and in the last month of follow-up.

Progression to Liver Transplant

Patients who become seronegative for HBV DNA in two (2) consecutive monthly tests may qualify as candidates for OLT.

What is claimed is:

1. A method of treating a Hepatitis B patient having hepatic decompensation, comprising administering Hepatitis B virus-reducing amounts of $T\alpha_1$ to a patient having decompensated liver disease so as to render said patient seronegative for Hepatitis B virus DNA.

2. The method of claim 1 wherein said $T\alpha_1$ is administered in a dosage amount within the range of about 0.4–4 mg.

3. The method of claim 1 wherein said $T\alpha_1$ is administered in a dosage amount within the range of about 1–4 mg.

4. The method of claim 1 wherein said $T\alpha_1$ is administered in a dosage amount of about 1.6 mg.

5. The method of claim 1 wherein said $T\alpha_1$ is administered to said patient two times weekly by subcutaneous injection.

6. The method of claim 1 wherein said patient has chronic Hepatitis B infection.

7. The method of claim 1 wherein said patient has chronic active Hepatitis B infection.

8. The method of claim 1 further including the steps, after rendering said patient seronegative for Hepatitis B virus DNA, of removing the patient's decompensated liver and then transplanting into the patient a healthy liver.

* * * * *